(12) United States Patent
Brown et al.

(10) Patent No.: US 8,268,005 B2
(45) Date of Patent: Sep. 18, 2012

(54) POROUS TITANIUM MODULAR REVISION PATELLA SYSTEM

(75) Inventors: David R. Brown, Warsaw, IN (US); Mark A. Bollinger, Fort Wayne, IN (US); Brian M. May, Warsaw, IN (US); Audra Watson, Ft. Wayne, IN (US)

(73) Assignee: Biomet Manufacturing Corp., Warsaw, IN (US)

( * ) Notice: Subject to any disclaimer, the term of this patent is extended or adjusted under 35 U.S.C. 154(b) by 245 days.

(21) Appl. No.: 12/697,851

(22) Filed: Feb. 1, 2010

(65) Prior Publication Data
US 2010/0131068 A1 May 27, 2010

Related U.S. Application Data

(62) Division of application No. 11/434,464, filed on May 15, 2006, now Pat. No. 7,691,149.

(51) Int. Cl.
*A61F 2/38* (2006.01)
*A61F 2/30* (2006.01)
(52) U.S. Cl. .............. 623/20.2; 623/18.11; 623/20.15
(58) Field of Classification Search ........... 623/14.12, 623/20.14–20.34; 606/232
See application file for complete search history.

(56) References Cited

U.S. PATENT DOCUMENTS

| | | |
|---|---|---|
| 3,927,423 A | 12/1975 | Swanson |
| 3,964,106 A | 6/1976 | Hutter, Jr. et al. |
| 4,041,550 A | 8/1977 | Frazier |
| 4,158,894 A | 6/1979 | Worrell |
| 4,759,768 A | 7/1988 | Hermann et al. |
| 4,913,157 A | 4/1990 | Pratt, Jr. et al. |
| 5,011,496 A | 4/1991 | Forte et al. |
| 5,019,104 A | 5/1991 | Whiteside et al. |
| 5,181,924 A | 1/1993 | Gschwend et al. |
| 5,197,986 A | 3/1993 | Mikhail |
| 5,236,461 A | 8/1993 | Forte |
| 5,236,462 A | 8/1993 | Mikhail |
| 5,358,529 A | 10/1994 | Davidson |
| 5,383,937 A | 1/1995 | Mikhail |
| 5,405,395 A | 4/1995 | Coates |
| 5,425,775 A | 6/1995 | Kovacevic et al. |

(Continued)

FOREIGN PATENT DOCUMENTS

EP 0307654 A2 3/1989

(Continued)

OTHER PUBLICATIONS

Augmentation Patella, Zimmer, http://www.zimmer.com/ctl?template=MP&action=&id=698&op=global&pr=Y (printed Mar. 8, 2006).

(Continued)

*Primary Examiner* — Paul Prebilic
*Assistant Examiner* — Andrew Iwamaye
(74) *Attorney, Agent, or Firm* — Harness, Dickey

(57) ABSTRACT

A patellar implant includes a posterior portion and an anterior portion. The posterior portion can have a first radial sidewall that extends between an outboard face and an inboard face. The outboard face can include an articulating surface. The inboard face can include one of a stem and a recess, and one of an annular central hub and an annular radial pocket. The anterior portion can have a second radial sidewall that extends between a tissue engaging surface and a posterior portion engaging surface.

17 Claims, 11 Drawing Sheets

U.S. PATENT DOCUMENTS

| | | | |
|---|---|---|---|
| 5,480,443 A | 1/1996 | Elias | |
| 5,522,901 A | 6/1996 | Thomas et al. | |
| 5,571,196 A | 11/1996 | Stein | |
| 5,609,640 A | 3/1997 | Johnson | |
| 5,609,644 A | 3/1997 | Ashby et al. | |
| 5,658,348 A | 8/1997 | Rohr, Jr. | |
| 5,702,465 A * | 12/1997 | Burkinshaw | 623/20.2 |
| 5,702,467 A | 12/1997 | Gabriel et al. | |
| 5,725,591 A | 3/1998 | DeCarlo, Jr. et al. | |
| 5,876,455 A | 3/1999 | Harwin | |
| 5,885,298 A | 3/1999 | Herrington et al. | |
| 5,951,603 A * | 9/1999 | O'Neil et al. | 623/20.33 |
| 5,957,979 A * | 9/1999 | Beckman et al. | 623/20.33 |
| 6,010,534 A * | 1/2000 | O'Neil et al. | 623/20.34 |
| 6,053,945 A * | 4/2000 | O'Neil et al. | 623/20.32 |
| 6,146,423 A | 11/2000 | Cohen et al. | |
| 6,315,798 B1 * | 11/2001 | Ashby et al. | 623/20.17 |
| 6,416,553 B1 | 7/2002 | White et al. | |
| 6,572,655 B1 | 6/2003 | Johnson | |
| 6,602,292 B2 | 8/2003 | Burkinshaw | |
| 6,616,696 B1 | 9/2003 | Merchant | |
| 6,620,198 B2 | 9/2003 | Burstein et al. | |
| 6,702,821 B2 | 3/2004 | Bonutti | |
| 6,770,078 B2 | 8/2004 | Bonutti | |
| 6,800,094 B2 * | 10/2004 | Burkinshaw | 623/20.18 |
| 6,855,150 B1 | 2/2005 | Linehan | |
| 6,923,831 B2 * | 8/2005 | Fell et al. | 623/14.12 |
| 7,048,741 B2 | 5/2006 | Swanson | |
| 2002/0072802 A1 * | 6/2002 | O'Neil et al. | 623/20.33 |
| 2002/0128719 A1 | 9/2002 | Burkinshaw | |
| 2003/0060883 A1 * | 3/2003 | Fell et al. | 623/14.12 |
| 2003/0088315 A1 * | 5/2003 | Supinski | 623/20.2 |
| 2003/0125745 A1 | 7/2003 | Tseng et al. | |
| 2004/0064192 A1 | 4/2004 | Bubb | |
| 2004/0143336 A1 | 7/2004 | Burkinshaw | |
| 2004/0143337 A1 * | 7/2004 | Burkinshaw | 623/20.18 |
| 2004/0236428 A1 * | 11/2004 | Burkinshaw et al. | 623/20.15 |
| 2005/0033424 A1 * | 2/2005 | Fell | 623/14.12 |
| 2005/0177240 A1 | 8/2005 | Blain | |
| 2006/0100714 A1 | 5/2006 | Ensign | |
| 2006/0241776 A1 | 10/2006 | Brown et al. | |
| 2006/0241781 A1 | 10/2006 | Brown et al. | |
| 2007/0129809 A1 | 6/2007 | Meridew et al. | |
| 2007/0135924 A1 * | 6/2007 | Verhoogen | 623/18.11 |
| 2007/0173948 A1 | 7/2007 | Meridew et al. | |
| 2007/0196230 A1 | 8/2007 | Hamman et al. | |
| 2007/0250175 A1 | 10/2007 | Meridew et al. | |
| 2007/0265708 A1 | 11/2007 | Brown et al. | |
| 2008/0147187 A1 | 6/2008 | Bollinger et al. | |
| 2009/0084491 A1 | 4/2009 | Uthgenannt et al. | |
| 2010/0057211 A1 | 3/2010 | Cuckler et al. | |

FOREIGN PATENT DOCUMENTS

FR 2642301 A1 8/1990

OTHER PUBLICATIONS

European Search Report mailed Nov. 20, 2009 for EP09169382 claiming benefit of U.S. Appl. No. 12/203,575, filed Sep. 3, 2008.
NexGen All Poly Patella, Zimmer, Inc., Mar. 8, 2006 (1 page).
NexGen Complete Knee Solution System—"Primary Porous Patella with Trabecular Metal" copyright 2001 Zimmer, Inc., (2 sheets).

* cited by examiner

POROUS TITANIUM MODULAR REVISION PATELLA SYSTEM

CROSS-REFERENCE TO RELATED APPLICATIONS

This application is a divisional of U.S. patent application Ser. No. 11/434,464 filed on May 15, 2006, issued as U.S. Pat. No. 7,691,149 on Apr. 6, 2010. The entire disclosure of the above application is incorporated herein by reference.

FIELD

This invention relates generally to a method and apparatus for use in patella revision surgery, and more particularly, to a method and apparatus for implanting a modular patellar implant having a polyethylene portion and a porous metal portion.

BACKGROUND

The patella is generally a flat, triangular bone located on the front of the knee joint. It is supported in the tendon of the quadriceps. The patella serves to protect the front of the knee and increase the leverage of the quadriceps.

During certain forms of surgery involving the knee, such as the implantation of a knee joint prosthesis, the natural patella may be resected for subsequent implantation of an artificial patella component. In one example, a patellar implant may be formed entirely of polyethylene. In some instances however, it may be difficult to stabilize such an implant relative to the surrounding tissue because a polyethylene surface may not be conducive to bone or soft tissue ingrowth. Consequently, securement of an entirely polyethylene patellar implant to a host patella may rely entirely on external fasteners such as sutures.

In another example, a patellar implant may comprise a polyethylene component having a porous metal backing secured by bone cement. In some cases however, the use of bone cement may present drawbacks. Application of bone cement may require careful placement and accuracy when locating the adhesive. Such a requirement may increase having excess bone cement entering the surrounding tissue and increase the surgery time.

SUMMARY

A patellar implant includes a posterior portion and an anterior portion. The posterior portion can have a first radial sidewall that extends between an outboard face and an inboard face. The outboard face can include an articulating surface. The inboard face can include one of a stem and a recess, and one of an annular central hub and an annular radial pocket. The anterior portion can have a second radial sidewall that extends between a tissue engaging surface and a posterior portion engaging surface.

The anterior portion can be formed of porous metal and have the other of the stem and the recess. The stem and the recess can attain a mechanical interlock in an assembled position upon advancement of the stem into the recess. The anterior portion can further have the other of the annular central hub and the annular radial pocket. Complementary engaging surfaces can be formed on the annular central hub and the annular radial pocket, respectively. The complementary engaging surfaces can surround the stem and the recess and engage each other when the annular radial pocket receives the annular central hub in the assembled position.

The anterior portion can have passages formed from the second radial sidewall to the tissue engaging surface. The passages can be adapted to pass a suture therethrough. The mechanical interlock between the stem and the recess, as well as engagement of the complementary engaging surfaces of the annular central hub and the annular radial pocket cooperate to resist separation of the posterior and anterior portions.

According to other features, the stem can be formed on the posterior portion. The stem can include a proximal end that extends from a body, an intermediate portion and a distal end. A radius of the stem can increase from the intermediate portion to the distal end. A recess can be formed in the anterior portion from the inboard surface of the anterior portion through an intermediate area to a terminal end. The stem can be integrally formed with the posterior portion and the recess can be integrally formed with the anterior portion.

According to other features, the posterior portion can include one of a protrusion and a depression that extends from the annular central hub or the annular radial pocket along the inboard face. The protrusion can comprise at least two protrusions. The depression can comprise at least two depressions. According to other features, the at least two protrusions can include radial outset members on one of the posterior portion and the anterior portion. The at least two depressions can define radial inset members on the other of the posterior portion and the anterior portion. The posterior portion can be formed of polyethylene.

According to still other features, the posterior portion can define a pair of blind bores that extend from the articulating surface toward the inboard face and are separated by a bridge that is recessed into the posterior portion from the outboard face. In one example, at least one of the complementary engaging surfaces can be tapered.

Further areas of applicability of the present disclosure will become apparent from the detailed description provided hereinafter. It should be understood that the detailed description and various examples, while indicating various embodiments of the invention, are intended for purposes of illustration only and are not intended to limit the scope of the following claims.

BRIEF DESCRIPTION OF THE FIGURES

The present invention will become more fully understood from the detailed description and the accompanying drawings, wherein:

FIG. 9 is an exploded perspective view of the modular patella system of FIG. 7 shown with the polyethylene component tilted for illustration;

FIG. 10 is a sectional view of the modular patella system taken along line 10-10 of FIG. 7;

DETAILED DESCRIPTION OF VARIOUS EMBODIMENTS

Figure 1:
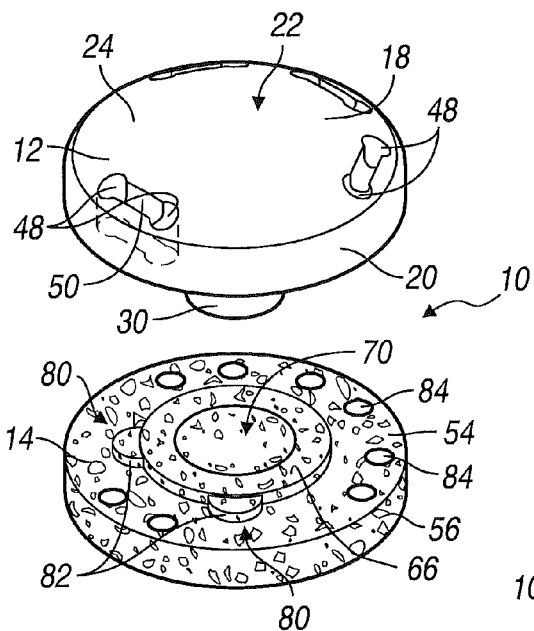
FIG. 1 is an exploded perspective view of a modular patella system including a polyethylene component and a porous metal component according to the present teachings.
Figure 2:
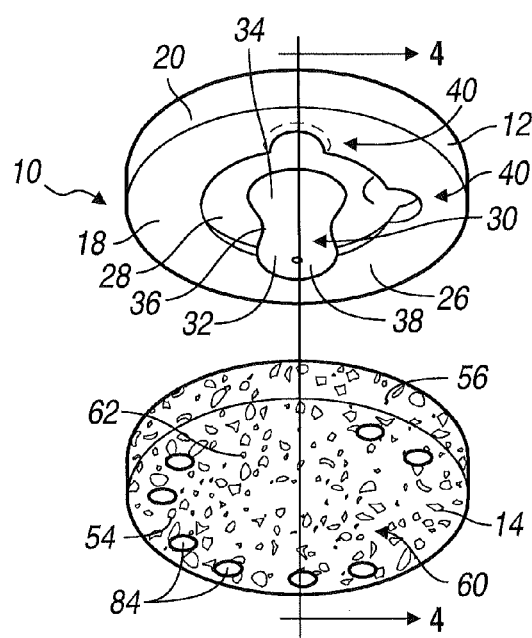
FIG. 2 is another exploded perspective view of the modular patella system of FIG. 1 illustrating an inboard face of the polyethylene component.

The following description of various embodiment(s) is merely exemplary in nature and is in no way intended to limit the application or uses.

With initial reference to FIGS. 1-6, a modular patella system according to a first example is shown and identified generally at reference numeral 10. The modular patella system 10 generally includes a posterior portion 12 and an anterior portion 14. The posterior portion 12 may be formed of polyethylene. The anterior portion 14 may be formed of porous metal such as titanium for example. As will be described, the modular patella system 10 may be used for patella revision surgery where minimal existing bone is present, or where no useful existing patella remains. In cases where healthy patella remains, but the bone is too shallow or otherwise unsuitable, the modular patella system may be adapted to be attached to the posterior surface of the shallow existing patella bone. In some instances it may be necessary to ream the existing patella bone to create a smooth complementary engagement surface. In cases where a patella is not suitable for attachment with the modular patella system, the patella may be removed entirely and the modular patella system attached to surrounding tissue such as to the patellar tendon.

With continued reference to FIGS. 1-6, the posterior portion 12 will be described in greater detail. The posterior portion 12 generally includes a body 18 having a radial sidewall 20. A convex surface 22 (FIG. 1) may be defined on an anterior face 24. An inboard face 26 defines a central radial pocket 28. A first integrally formed retaining member 30 may extend from the inboard face 26 of the posterior portion 12. In the example shown, the first integrally formed retaining member 30 may include a stem 32. The stem 32 may generally define a proximal end 34 extending from the inboard face 26 of the body 18, an intermediate portion 36 and a distal end 38. As illustrated most clearly in FIG. 6, a radius of the stem 32 may generally increase from the intermediate portion 36 toward the distal end 38 and toward the proximal end 34.

A pair of anti-rotation elements 40 may be defined on the inboard face 26 of the posterior portion 12. In one example, the anti-rotation elements 40 may define depressions 42 (FIG. 3) formed in the inboard face 26 of the posterior portion 12. As illustrated most clearly in FIGS. 2 and 3, the depressions 42 may define radial inset members formed in the central radial pocket 28. In one example, the depressions 42 may extend from the inboard face 26 into the body 18 at a depth substantially equivalent to the central radial pocket 28.

A collection of passages 48 may be formed substantially through the body 18 of the posterior portion 12. More specifically, passages 48 may extend from the convex outer surface 22 toward the inboard face 26 of the posterior portion 12. In the example shown, the passages 48 do not extend entirely through the body 18. However, the passages 48 may alternatively pass entirely through the body 18. A bridge 50 (FIG. 1) may be defined between adjacent pairs of passages 48. As will become appreciated, the bridge 50 may provide an engagement surface when securing the modular patella system 10 to an implant site with sutures.

Figure 5:
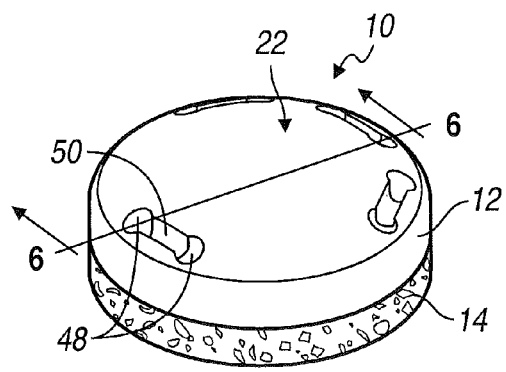
FIG. 5 is an assembled perspective view of the modular patella system of FIG. 1.
Figure 6:
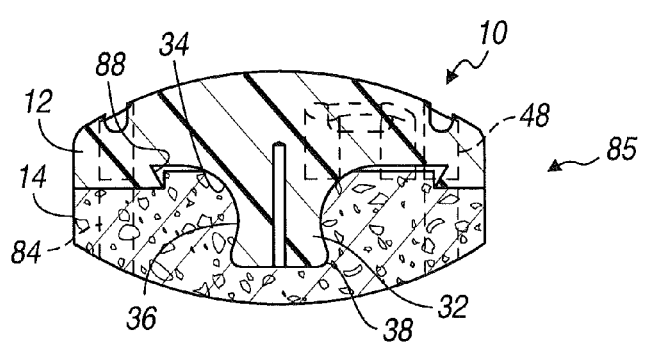
FIG. 6 is a sectional view of the modular patella system taken along line 6-6 of FIG. 5.
Figure 7:
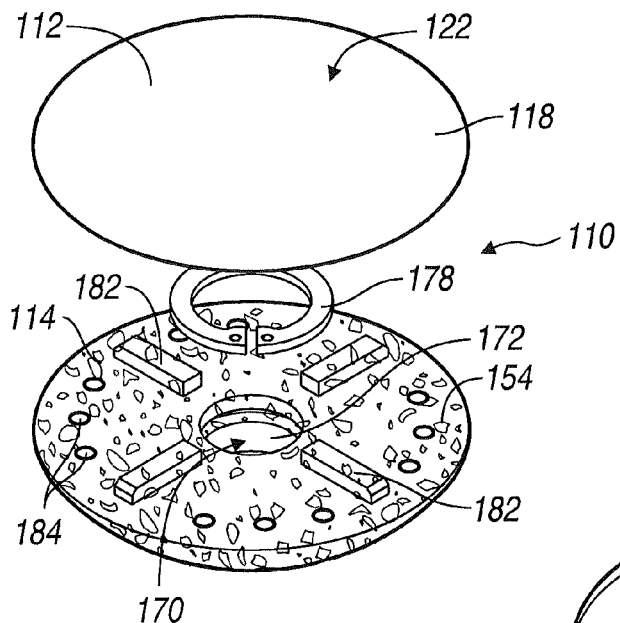
FIG. 7 is an exploded perspective view of a modular patella system including a polyethylene component and a porous metal component according to additional features of the present teachings.
Figure 8:
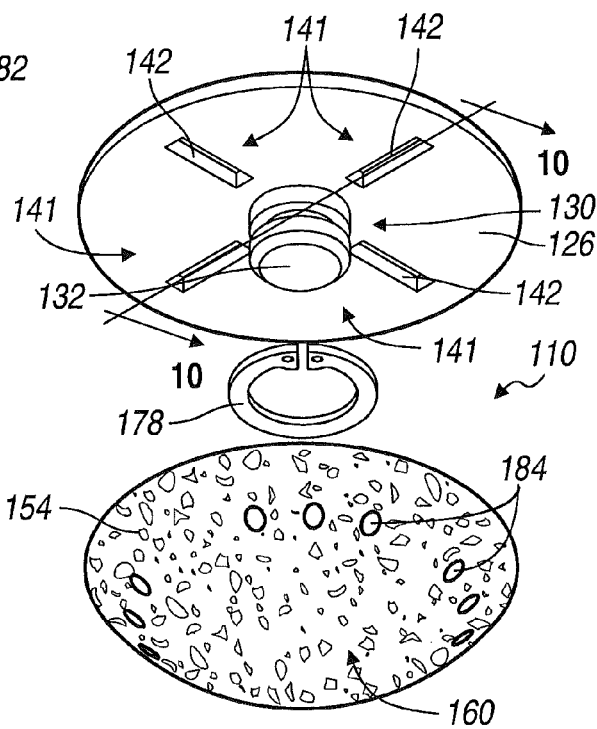
FIG. 8 is another exploded perspective view of the modular patella system of FIG. 7 illustrating an inboard face of the porous metal component.

With continued reference to FIGS. 1-6, the anterior portion 14 will be described in greater detail. The anterior portion 14 generally includes a body 54 having a radial sidewall 56. A convex surface 60 (FIG. 2) may be defined on an anterior face 62. An inboard face 64 may define a central hub 66. A second integrally formed retaining member 70 may be defined on the anterior portion 14. In the example shown, the second integrally formed retaining member 70 may be defined by a recess 72 formed in the anterior portion 14. As most clearly illustrated in FIGS. 4 and 5, the recess 72 may be defined from the inboard face 64 at the hub 72 through an intermediate area 74 to a terminal end 76. A radius defined by the recess 72 may increase from the intermediate area 74 to the terminal end 76 and to the inboard face 64. As will become appreciated, the first and second integrally formed retaining members 30 and 70 may define complementary shapes suitable to provide a press-fit relationship in an assembled position (FIG. 6). In other examples, the recess 72 and central hub 66 may be formed on the posterior portion 12 while the stem 32 and radial pocket 28 may be formed on the anterior portion 14. In still other examples, the stem 32 and the central hub 66 may be formed on the posterior portion 12 while the recess 72 and the radial pocket 28 may be formed on the anterior portion 14.

Figure 3:
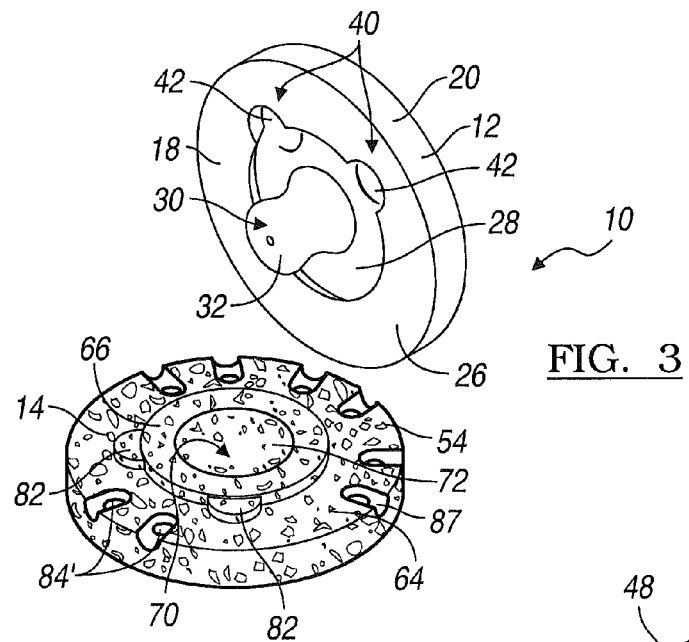
FIG. 3 is an exploded perspective view of the modular patella system of FIG. 1 shown with the polyethylene component tilted for illustration.

The anterior portion 14 further defines a pair of complementary anti-rotation elements 80 in the form of protrusions 82 extending from the inboard face 64 of the anterior portion 14. In an assembled position (FIG. 6), the protrusions 82 may nest within the depressions 42 formed in the posterior portion 12 to inhibit relative rotation of the posterior and anterior portions 12 and 14, respectively. In other examples, the radial outset members 82 may be formed on the posterior portion 12 while the radial inset members 42 may be formed on the anterior portion 14. The anterior portion 14 may define a series of passages 84 formed in locations to align with the collection of passages 48 in the posterior portion 12. As will be described in detail later, the passages 48 and 84, respectively, may be utilized to pass suture during attachment to surrounding bone and/or tissue. As shown in FIG. 3, alternate passages 84' may define a recesses 87 extending to the outer radial surface of the anterior portion 14 for protecting suture during use.

Figure 4:
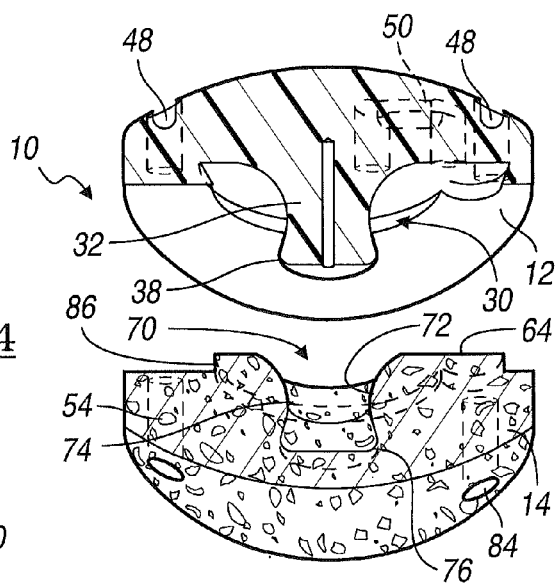
FIG. 4 is a sectional view of the modular patella system taken along line 4-4 of FIG. 2.

With specific reference now to FIGS. 4-6, assembly of the posterior and anterior portions 12 and 14 will now be described. At the outset, the stem 32 of the posterior portion 12 may be located proximate the recess 72 of the anterior portion 14 (FIG. 4). It may be necessary to at least partially align the respective anti-rotation features 40 and 80. Next, the stem 32 may be advanced in a direction defined by its longitudinal axis (in a direction downwardly as viewed in FIG. 4). A radius defined at the distal portion 38 of the stem 32 may be larger than a radius defined at the intermediate area 74 of the recess 72. As a result, as the stem 32 is advanced toward the terminal end 76 of the recess 72, the distal portion 38 of the stem 32 may contract slightly while passing through the intermediate area 74 of the recess 72. Once the distal end 38 of the stem 32 passes the intermediate area 74 of the recess 72, the distal end 38 of the stem 32 may be advanced to the terminal end 76 of the recess 72 (FIG. 6). At this point, the distal end 38 of the stem 32 may expand to its normal position defined by a radius larger than a radius defined by the intermediate area 74 of the recess 72. In this regard, the stem 32 may be retained by the recess 72 in a secure assembled position such that separation of the posterior and anterior portions 12 and 14 is inhibited. In the assembled position (FIG. 6) the posterior and anterior portions 12 and 14 collectively define a patellar implant 85 generally having a biconvex structure.

As most clearly shown in FIGS. 4 and 6, the central hub 66 and protrusions 82 of the anterior portion 14 may define a lateral sidewall 86. The central radial pocket 28 of the posterior portion 12 may define a tapered sidewall 88. In this way, the respective surfaces 86 and 88 may provide supplemental retaining capacity in the assembled position. It is appreciated that the porous material of the posterior portion 12 may slightly expand at the tapered sidewall 88 until the anterior portion 14 is provided adequate clearance during assembly of the posterior portion 12 and the anterior portion 14. In another example, the lateral sidewall 86 may also be tapered.

Turning now to FIGS. 7-12, a modular patella system according to a second example is shown and identified generally at reference numeral 110. As with the first modular patella system 10, the second example includes a posterior portion 112 and an anterior portion 114. The posterior portion 112 may be formed of polyethylene. The anterior portion 114 may be formed of porous metal such as titanium for example. Exemplary methods for making porous metal may be found in co-pending applications, U.S. Ser. No. 11/357,929, filed Feb. 17, 2006, entitled "Method and Apparatus for Forming Porous Metal Implants", U.S. Ser. No. 11/111,123 filed Apr. 21, 2005; Ser. No. 11/294,692, filed Dec. 5, 2005; and Ser. No. 11/357,868, filed Feb. 17, 2006), each entitled "Method and Apparatus for use of Porous Implants" and all also assigned to Biomet, Inc., of Warsaw Ind., which is incorporated herein by reference.

The modular patella system 110 may be used for patella revision surgery where minimal existing bone is present, or where no useful existing patella remains.

With continued reference to FIGS. 7-12, the posterior portion 112 will be described in greater detail. The posterior portion 112 may define a body 118 having a convex posterior face 122 and an inboard face 126. The inboard face 126 may include a first integrally formed retaining member 130. In the example shown, the first integrally formed retaining member 130 may include a stem 132. The stem 132 may generally define a proximal end 134 extending from the inboard face 126 of the body 118, an intermediate portion 136 and a distal end 138. A transition between the intermediate portion 136 and the distal end 138 may be defined by a tapered annular surface 139. The intermediate portion 136 may define a first annular pocket 140. Two pair of anti-rotation elements 141 may be defined on the inboard face 126 of the posterior portion 112. In the example shown, the anti-rotation elements 141 define depressions 142 in the form of rectangular cavities. It is appreciated that other geometries may be defined by the depressions 142.

The anterior portion 114 may generally include a body 154 having a convex anterior face 160 and an inboard face 164. A second integrally formed retaining member 170 may be defined on the anterior portion 114. In the example shown, the second integrally formed retaining member 170 may be defined by a recess 172 formed in the anterior portion 114. As most clearly shown in FIGS. 10 and 11, the recess 172 may be defined from the inboard face 164 through an intermediate area 174 to a terminal end 176. The intermediate area 174 may define a second annular pocket 177. The second annular pocket 177 may support a snap-ring 178 therein.

The anterior portion 114 may define two pair of complementary anti-rotation elements 180 in the form of rectangular protrusions 182 extending from the inboard face 164 of the anterior portion 114. In an assembled position 182, the protrusions may nest within the depressions 142 formed in the posterior portion 112 to inhibit relative rotation of the posterior and anterior portions 112 and 114, respectively. The anterior portion 114 may further define a series of passages 184 formed through the body 154. As will be described in detail later, the respective passages 184 may be utilized to pass suture or screws during attachment to surrounding bone and/or tissue.

Figure 11:
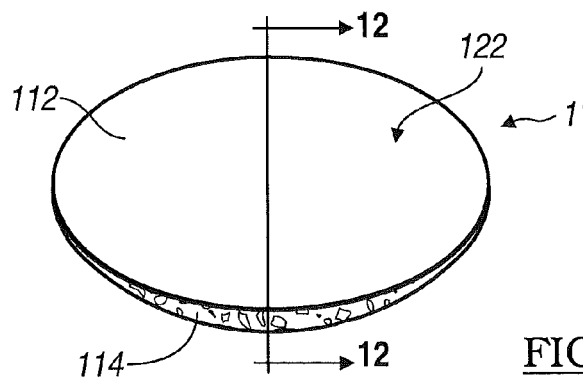
FIG. 11 is an assembled perspective view of the modular patella system of FIG. 7.
Figure 12:
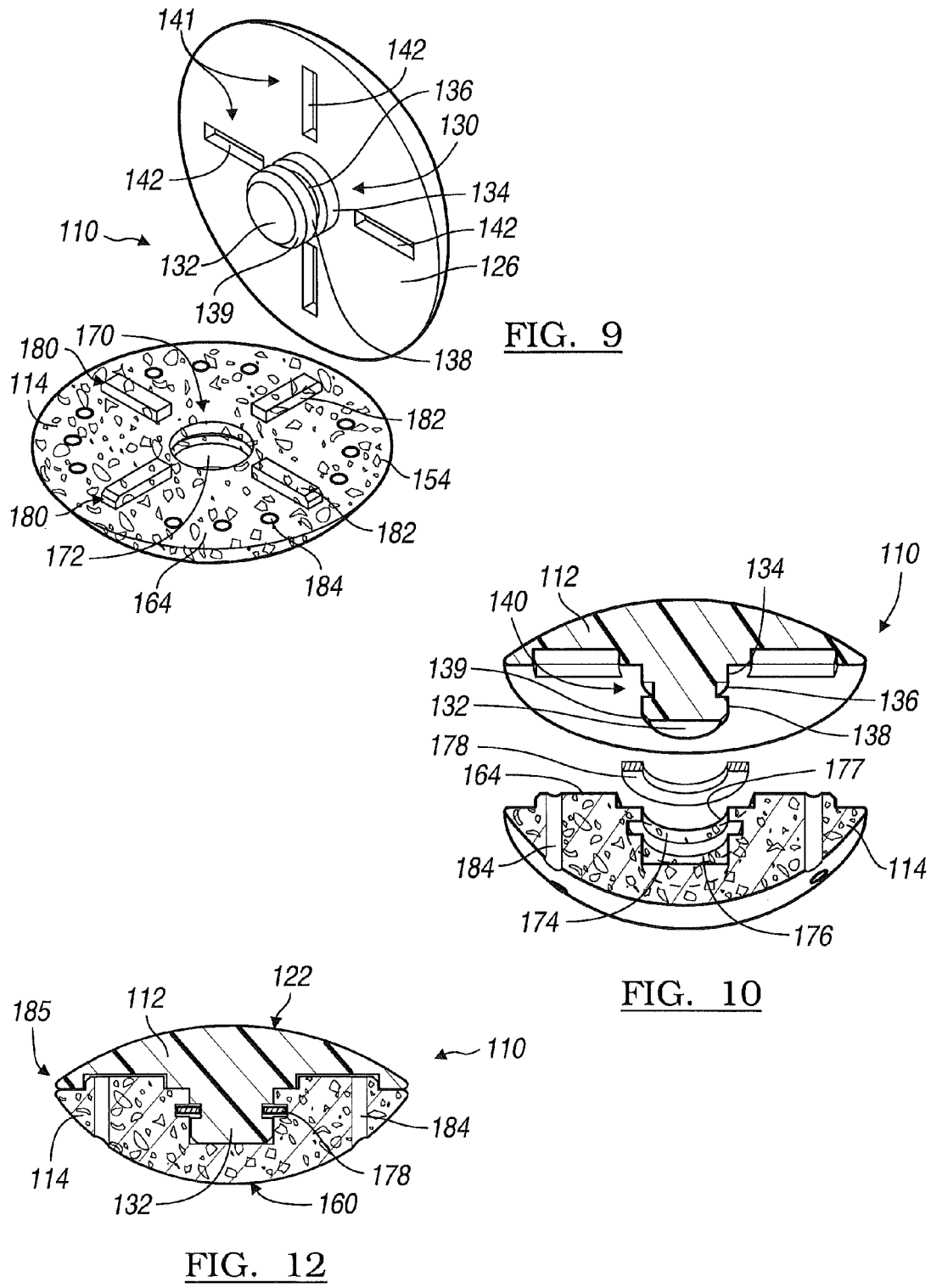
FIG. 12 is a sectional view of the modular patella system taken along line 12-12 of FIG. 11.

With specific reference now to FIGS. 10-12, assembly of the posterior and anterior portions 112 and 114 will now be described according to one example. At the outset, the stem 132 of the posterior portion 112 may be located proximate the recess 172 of the anterior portion 114. It may be necessary to at least partially align the respective anti-rotation features 141 and 180. Next, the stem 132 may be advanced in a direction defined by its longitudinal axis (in a direction downwardly as viewed in FIG. 10). As the stem 132 is inserted into the recess 172, the annular tapered surface 139 may slidably negotiate through the snap-ring 178 thereby urging the snap-ring 178 outwardly to accept the outer diameter of the distal portion 138. Once the first annular pocket 140 defined on the stem 132 aligns with the position of the snap-ring 178, the snap-ring 178 may contract to a static position (FIG. 12). In the static position, the snap-ring 178 may generally nest within an area defined by the first and second annular pockets 140 and 177. In the assembled position, the snap-ring 178 may resist axial movement of the stem 132 and therefore securely retain the posterior and anterior portions 112 and 114, respectively, together. The assembled posterior and anterior portions 112 and 114, respectively, are hereinafter referred to collectively as implant 185.

Figure 13:
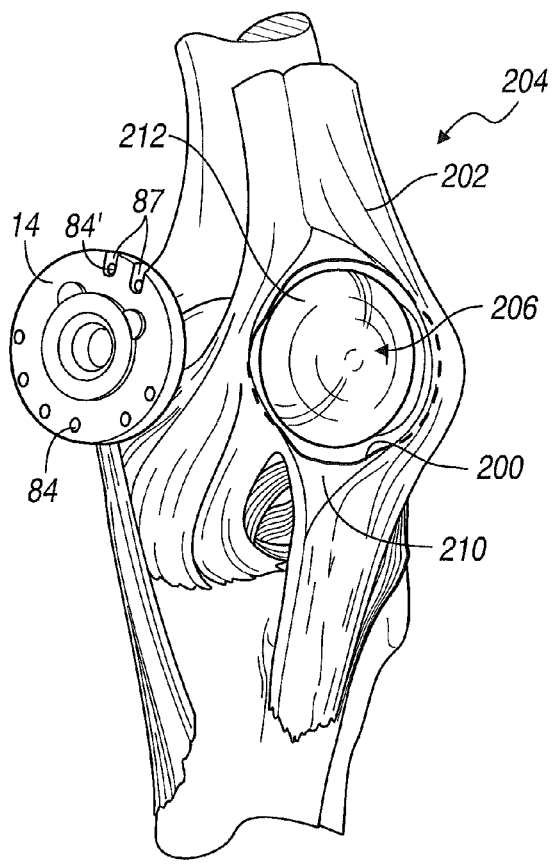
FIG. 13 illustrates an exemplary right knee having a host patella rotated laterally to gain access to a posterior patella face for implantation of an exemplary anterior portion according to a first example.
Figure 14:
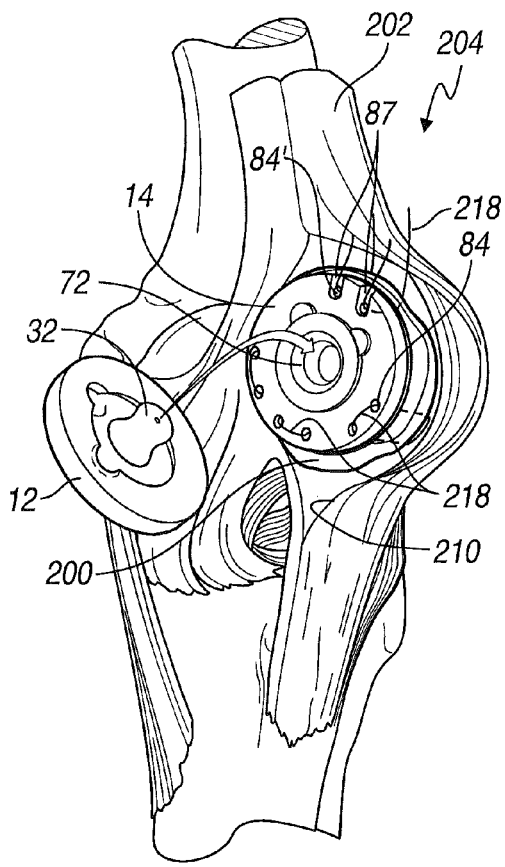
FIG. 14 illustrates an exemplary posterior portion being assembled onto the anterior portion according to the present teachings.
Figure 15:
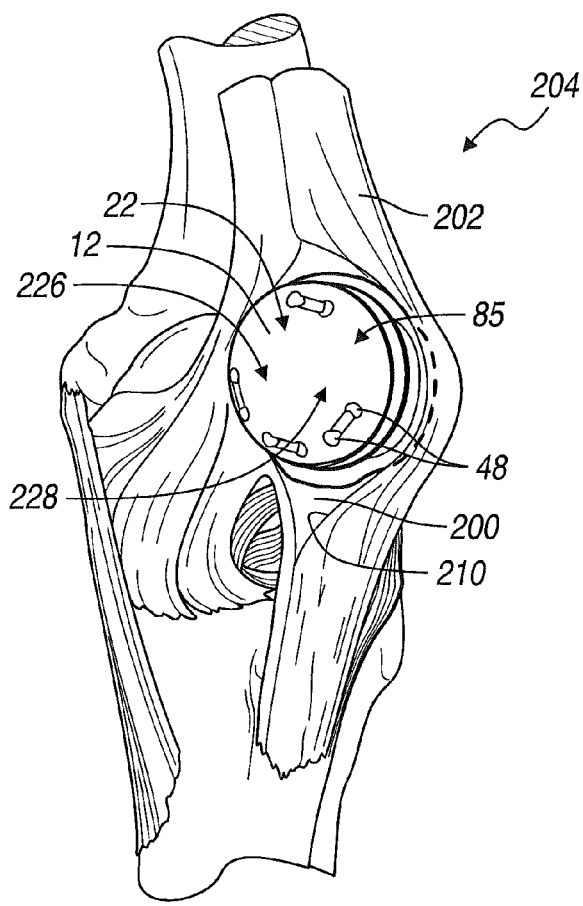
FIG. 15 illustrates the anterior and posterior portions in an assembled position implanted onto the posterior patella.

Turning now to FIGS. 13-16, a first exemplary method of implanting the modular patella system 10 of FIGS. 1-6 will be described. For clarity, in all FIGS. depicting steps for implanting the modular patella system, the anterior portion has been shown without the porous metal detail. It is appreciated, however, that each anterior portion may be comprised entirely of porous metal such as depicted in FIGS. 1-12. As described above, the modular patella system 10 may be used for patella revision surgery where minimal existing bone is present. As shown in FIG. 13, an existing patella 200 is shown within a patellar tendon 202 of a right knee 204. The exemplary patella 200 is generally shallow and suitable for attachment by the modular patella system 10.

In one example, the patella 200 may be rotated about a superior/inferior axis to gain access to a posterior surface 206 of the existing patella 200. In the example shown, the patella 200 is rotated laterally. To allow such rotation, it may be necessary to make an incision 210 in the patellar tendon 202. In some examples, the posterior patella 206 may be reamed to define a smooth concave posterior surface 212 complementary to the convex surface 60 of the anterior portion 14. According to a first example of implantation, the anterior portion 14 may be secured against the posterior surface 212 of the patella 200. Sutures 218 may be passed through any or all of the passages 84 provided in the anterior portion 14 to facilitate attachment. The sutures 218 may pass through holes formed in the patella 200 and/or surrounding tissue including the patellar tendon 202. While some of the passages are depicted as 84 and others 84', it is appreciated that the passages may comprise all passages 84, all passages 84' or any combination thereof. Other methods of attachment are contemplated, such as but not limited to, fasteners such as bone screws. In one example, the attachment structure, such as bone screws may be formed of resorbable material.

Figure 16:
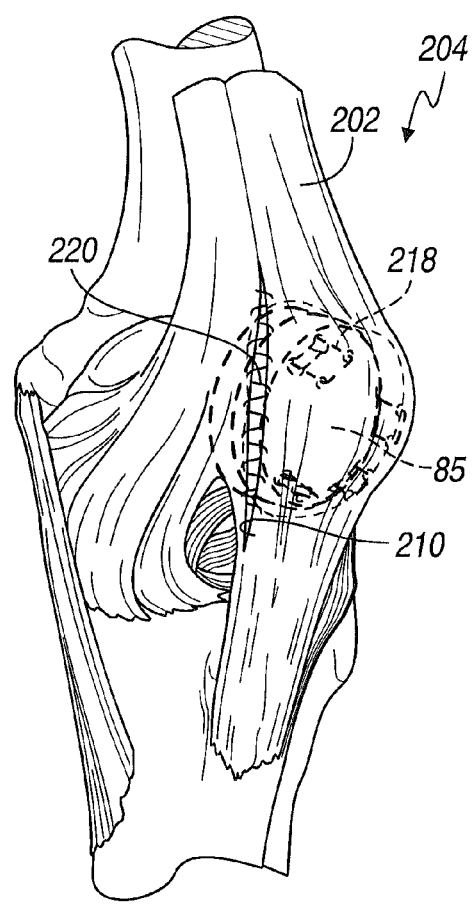
FIG. 16 illustrates the host patella and assembled implant of FIG. 15 rotated medially into an implanted position.
Figure 17:
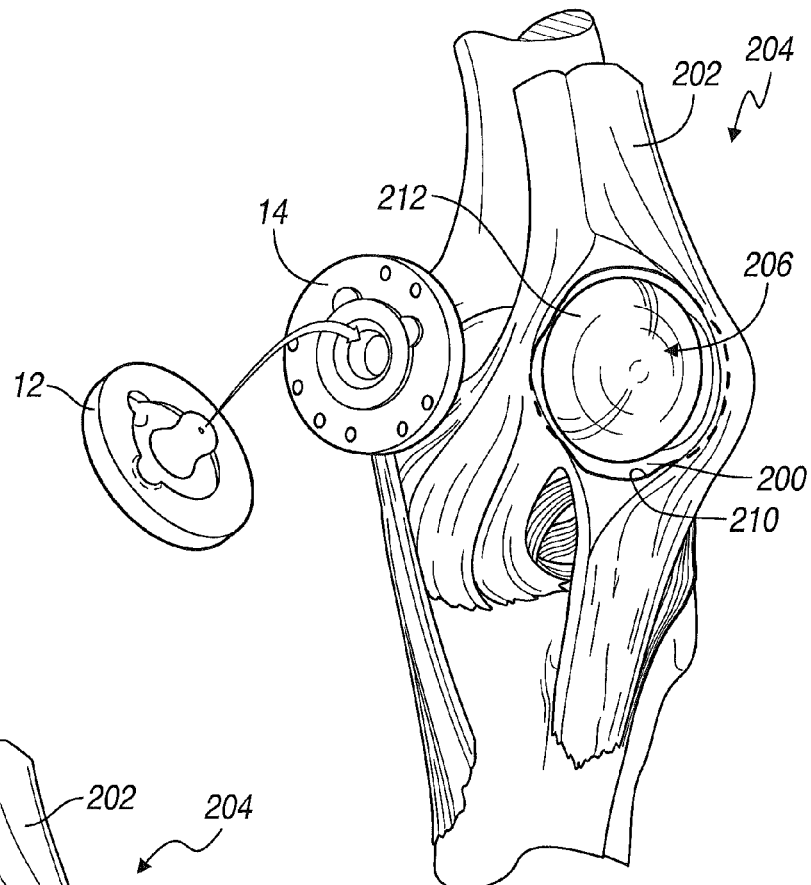
FIG. 17 illustrates an exemplary right knee having a host patella rotated laterally to gain access to a posterior patella face for implantation of pre-assembled anterior and posterior portion according to a second example.
Figure 18:
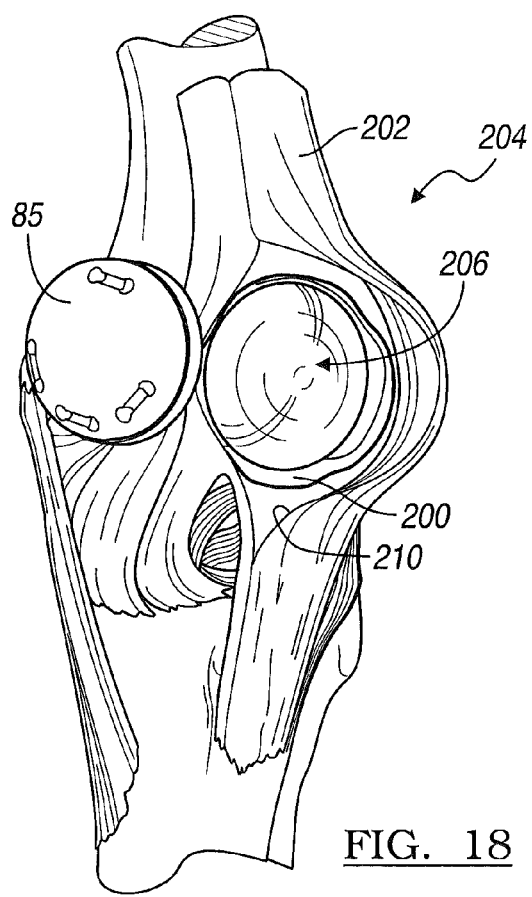
FIG. 18 illustrates a pre-assembled implant prior to implantation onto the posterior patella.
Figure 19:
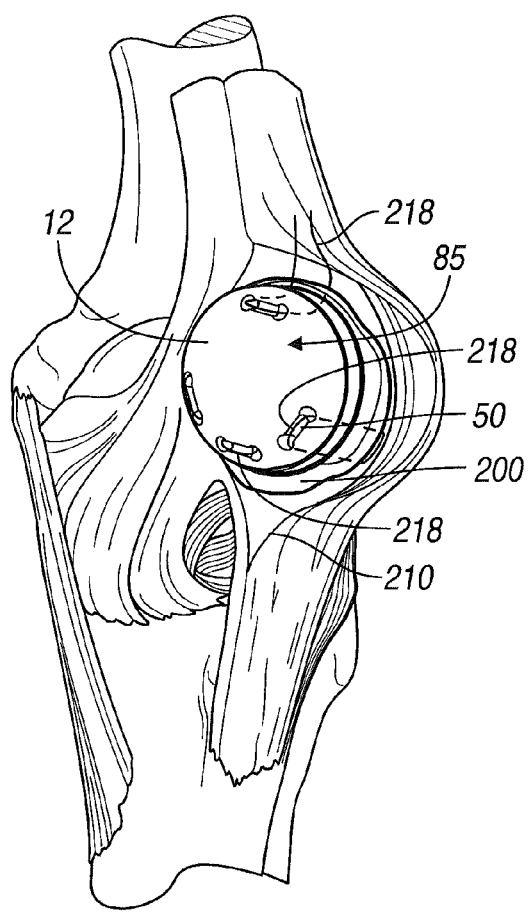
FIG. 19 illustrates the pre-assembled implant of FIG. 18 secured to the posterior patella.
Figure 20:
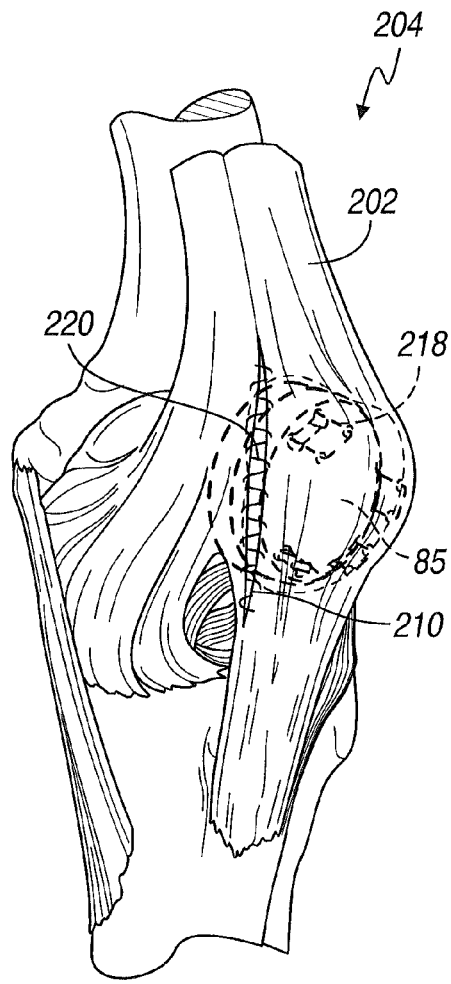
FIG. 20 illustrates the host patella and assembled implant of FIG. 19 rotated medially into an implanted position.
Figure 21:
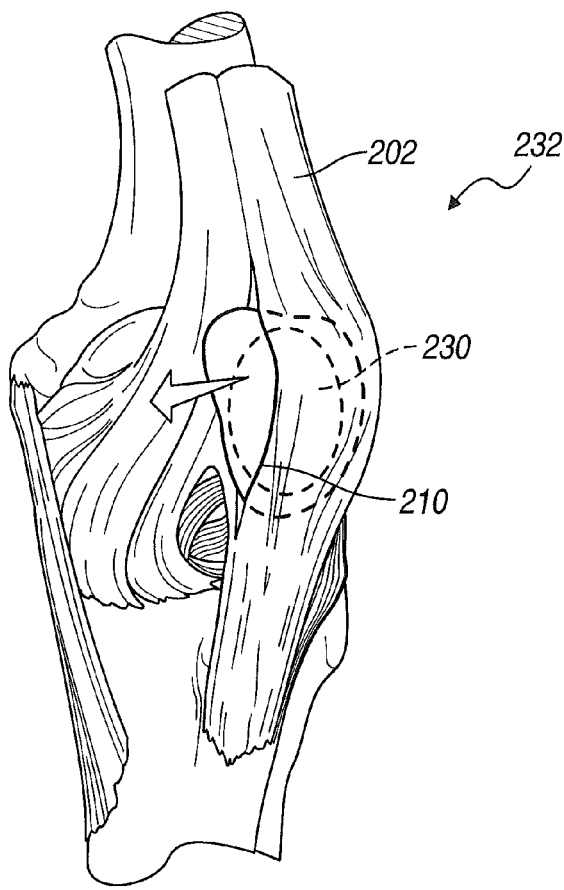
FIG. 21 illustrates an exemplary right knee having an unsuitable host patella being removed for implantation of a patellar implant according to additional features.
Figure 22:
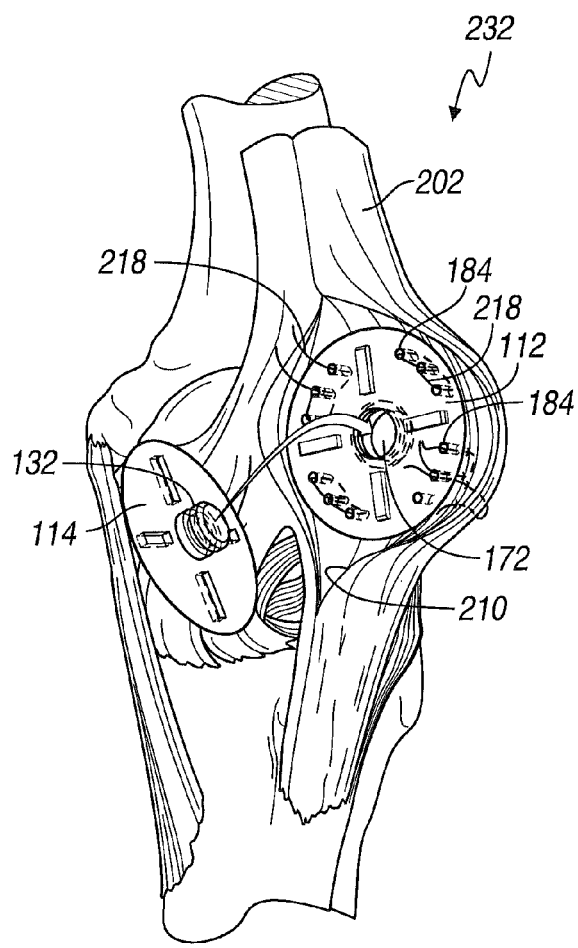
FIG. 22 illustrates an exemplary anterior portion secured to the patellar tendon for receipt of an exemplary posterior portion.
Figure 23:
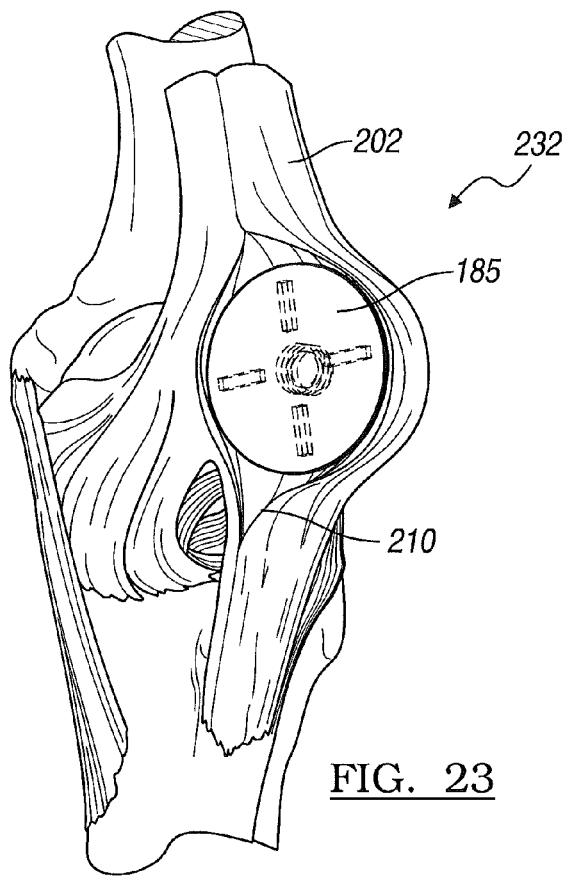
FIG. 23 illustrates the posterior portion assembled onto the anterior portion into an assembled position.

Once the anterior portion 14 is suitably attached to the patella 200, the stem 32 of the posterior portion 12 may be inserted into the recess 72 of the anterior portion 14 into an assembled position as described above. The implant 85 may then be rotated back to the original orientation of the patella 200 (FIG. 16). The incision 210 in the patellar tendon may then be closed such as by sutures 220. In an implanted position, a lateral portion 226 of the convex outer surface 22 of the posterior (polyethylene) portion 12 may be adapted for articulation with a lateral condyle of the femur (not shown). Likewise a medial portion 228 of the convex outer surface 22 of the posterior portion 12 may be adapted for articulation with a medial condyle of the femur (not shown).

While the above example has been described with respect to attachment to an existing patella 200, the same principles may be used to attach the anterior portion 14 directly to the surrounding tissue such as to the patellar tendon 202 in cases where an existing patella cannot be used.

In another example shown in FIGS. 17-20, the posterior and anterior portions 12 and 14 may be assembled together prior to implantation at the implant site. In such an example, the implant 85 may be secured to the existing patella 200 by way of sutures 218 passed through the passages on the posterior portion 12 and complementary passages on the anterior portion 14. The respective bridge portions 50 may provide a bearing surface for the sutures 218 in an attached position. It is appreciated in one example, some or all of the passages 48 may need to be pierced completely through the body 18 as needed.

Turning now to FIGS. 21-24, a first exemplary method of implanting the modular patella system 110 of FIGS. 7-12 will be described. The anterior portion 114 may be implanted at the implant site precedent to assembly with the posterior portion 112. In the exemplary FIGS. 21-24 shown, the existing patella 230 of a knee joint 232 was not suitable for implant attachment and therefore, has been removed. As a result, the anterior portion 114 may be secured such as by sutures 218 through some or all of the passages 184 to the surrounding tissue such as the patellar tendon 202.

Figure 24:
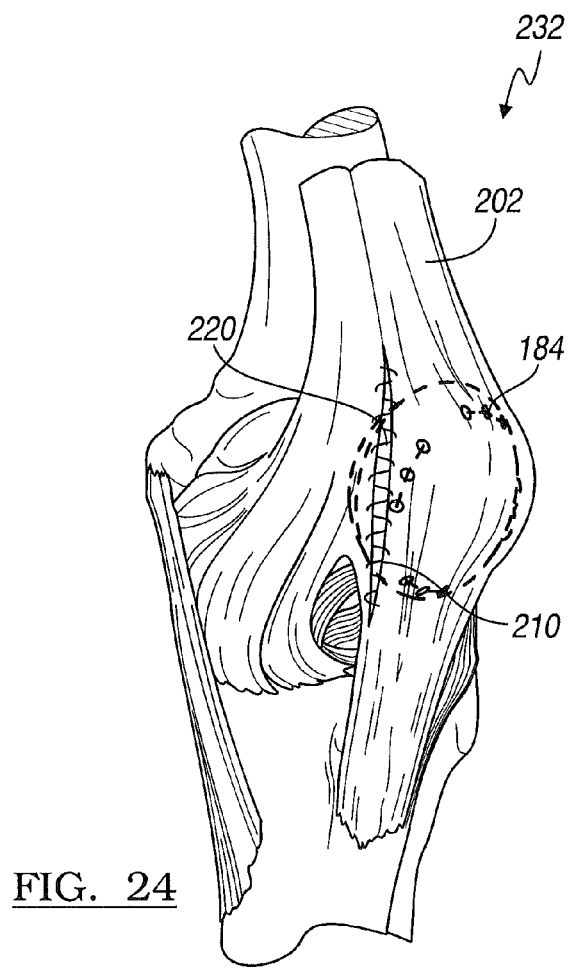
FIG. 24 illustrates the assembled implant rotated medially into an implanted position.

In this way, once the anterior portion 114 has been suitably secured at the attachment site, the stem 132 may be subsequently inserted into the recess 172 until the snap-ring 178 (not specifically shown) captures the posterior and anterior portions together as described in greater detail above. Once the posterior and anterior portions 112 and 114 have been assembled, the implant 185 may be placed in the desired location relative to the surrounding bone and tissue (FIG. 24). Again, while this particular example has been shown implanted at an implant site wherein a patella has been removed, the same principles may be applied to implanting the modular patella system 110 to a shallow existing patella using similar steps outlined above with respect to the modular patella system.

In all of the examples described above and otherwise contemplated by the present teachings, the porous metal located anteriorly on the implant may encourage bone and tissue ingrowth, such as with an existing patella and/or patellar tendon. The polyethylene located proximally on the implant may provide a smooth articulation surface to complement the respective condyles of the femur.

It is contemplated that a set comprised of various diameters and thicknesses of cooperating posterior and anterior portions may be provided. In this way, a surgeon may select one posterior portion from a collection of posterior portions suitable for the particular patient. Likewise, a surgeon may select one anterior portion from a collection of anterior portions according to the particular needs of the patient. In all posterior and anterior portions however, the complementary mating features, i.e., the integrally formed retaining features and anti-rotation features may be equivalent to support such interchangeability.

Figures 25, 26, 27:
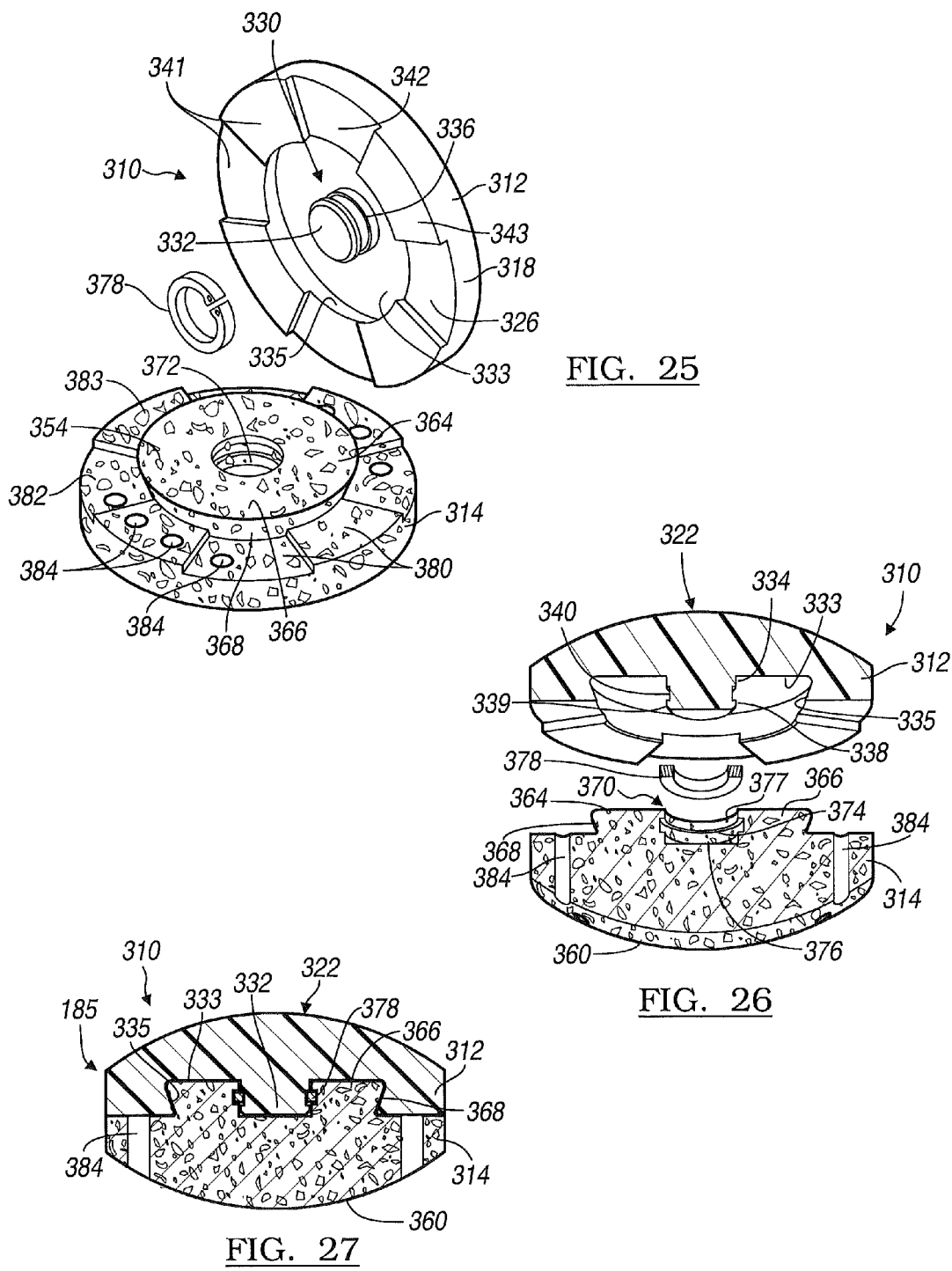
FIG. 25 is an exploded perspective view of a modular patella system including a polyethylene component and a porous metal component according to additional features of the present teachings.
FIG. 26 is a sectional view of the modular patella system of FIG. 25.
FIG. 27 is a sectional view of the modular patella system of FIG. 26 shown in an assembled position.

A modular patella system according to a third example and identified at reference numeral 310 in FIGS. 25-27. As with the first and second examples 10 and 110, the third example includes a posterior portion 312 and an anterior portion 314. For simplicity, like reference numerals of the third example 310 have been used to denote like features of the second example 110. The anterior portion 314 may be formed of porous metal such as titanium for example. Again, the modular patella system 310 may be used for patella revision surgery where minimal existing bone is present, or where no useful existing patella remains.

The posterior portion 312 may define a body 318 having a convex posterior face 322 and an inboard face 326. In one example, the convex posterior face 322 can be uniformly convex. The inboard face 326 may include a first integrally formed retaining member 330. In the example shown, the first integrally formed retaining member 330 may include a stem 332. The stem 332 is generally configured similar to the stem 132 (FIGS. 8-12). The body 318 can also include an annular radial pocket 333 that surrounds the stem 332. The annular radial pocket 333 can be formed by a continuous tapered surface 335.

Anti-rotation elements 341 may be defined on the inboard face 326 of the posterior portion 312. In the example shown, the anti-rotation elements 141 define a collection of depressions and extensions 342 and 343, respectively.

The anterior portion 314 may generally include a body 354 having a convex anterior face 360 and an inboard face 364. The body 354 can include an annular central hub 366 having a continuous tapered surface 368. In one example, the convex anterior face 360 can be uniformly convex. A second integrally formed retaining member 370 may be defined on the anterior portion 314. In the example shown, the second integrally formed retaining member 370 may be defined by a recess 372 formed in the anterior portion 314. As shown in FIG. 26, the recess 372 may be defined from the inboard face 364 through an intermediate area 374 to a terminal end 376. The intermediate area 374 may define a second annular pocket 377. The second annular pocket 377 may support a snap ring 378 therein.

The anterior portion 314 may define a series of complementary anti-rotation elements 380. In the example shown, the anti-rotation elements 380 define a collection of depressions and extensions 382 and 383, respectively. The depressions and extensions 342 and 343 of the posterior portion 312 are adapted to cooperatively mate with the depressions and extensions 382 and 383 of the anterior portion 314 in an assembled position (FIG. 27). Steps for assembling the posterior and anterior portions 312 and 314 are substantially similar to those described with respect to the modular patella system 110. Likewise, a method of implanting the modular patella system 310 is substantially similar to the method described in relation to the modular patella system 110.

In another example it is contemplated that the integrally formed retaining features may also provide anti-rotation characteristics. In this way, the anti-rotation features may be formed with the integrally formed retaining features instead of separately. In other examples, it is envisioned that the stem and recess may define shapes other than cylindrical. Some exemplary shapes may include oval, rectangular, triangular, octagonal and others. In such an example, the respective surfaces defined by the stem and recess may discourage rotation of the stem within the recess providing an anti-rotation feature between the proximal and anterior portions.

Those skilled in the art can now appreciate from the foregoing description that the broad teachings of the present invention can be implemented in a variety of forms. For example, while the posterior portion has been described as having the stem and the anterior portion has been described as defining the recess, one skilled in the art will appreciate that the respective features may be swapped. Furthermore, the respective integrally formed retaining features may define other structures suitable for interconnection. In one example, a threaded male portion may be defined on one of the posterior and anterior portions and a grooved female portion may be defined on the other portion. Other configurations are contemplated. In addition, while the respective anterior portions have been described as porous metal, they may alternatively comprise solid metal having a porous coating. The articulation surface may alternatively comprise ceramic, a ceramic-like isotropic coating over a graphite substrate, cobalt-chromium compounds. Therefore, while this invention has been described in connection with particular examples thereof, the true scope of the invention should not be so limited since other modifications will become apparent to the skilled practitioner upon a study of the drawings, the specification and the following claims.

What is claimed is:

1. A patellar implant comprising:
    a posterior portion having a first radial sidewall extending between an outboard face and an inboard face, said outboard face including an articulating surface, said inboard face including one of a stem and a recess, and one of an annular central hub and an annular radial pocket said posterior portion further defining a pair of blind bores that extend from said articulating surface toward said inboard face and are separated by a bridge that is recessed into said posterior portion from said outboard face;
    an anterior portion having a second radial sidewall extending between a tissue engaging surface and a posterior portion engaging surface, said anterior portion being formed of porous metal and having the other of said stem and said recess wherein said stem and said recess attain a mechanical interlock in an assembled position upon advancement of said stem into said recess, said anterior portion further having the other of said annular central hub and said annular radial pocket, wherein complementary engaging surfaces formed on said annular central hub and said annular radial pocket, respectively, surround said stem and said recess and engage each other when said annular radial pocket receives said annular central hub in said assembled position, said anterior portion having passages formed from said second radial sidewall to said tissue engaging surface, said passages adapted to pass suture therethrough; and
    wherein said mechanical interlock between said stem and recess, as well as engagement of said complementary engaging surfaces of said annular central hub and said annular radial pocket cooperate to resist separation of said posterior and anterior portions.

2. The patellar implant of claim 1 wherein said stem is formed on said posterior portion and includes a proximal end extending from a body, an intermediate portion and a distal end, wherein a radius of said stem increases from said intermediate portion to said distal end.

3. The patellar implant of claim 2 wherein said recess is formed in said anterior portion, from said posterior portion engaging surface of said anterior portion through an intermediate area to a terminal end.

4. The patellar implant of claim 2 wherein said stem is integrally formed with said posterior portion and said recess is integrally formed with said anterior portion.

5. The patellar implant of claim 1 wherein said posterior portion includes one of a protrusion and a depression that extends from said annular central hub or said annular radial pocket along said inboard face.

6. The patellar implant of claim 5 wherein said protrusion comprises at least two protrusions and wherein said depression comprises at least two depressions.

7. The patellar implant of claim 6 wherein said at least two protrusions include radial outset members on one of said posterior portion and said anterior portion and wherein said at least two depressions define radial inset members on the other of said posterior portion and said anterior portion.

8. The patellar implant of claim 1 wherein said posterior portion is formed of polyethylene.

9. The patellar implant of claim 1 wherein at least one of said complementary engaging surfaces are tapered.

10. A patellar implant comprising:
    a polyethylene portion having a uniformly convex posterior articulating surface and a first inboard surface, said first inboard surface having a first integrally formed retaining feature comprising one of a stem and recess centrally formed thereon, said first inboard surface further comprising one of an annular central hub and an annular radial pocket that surrounds said first integrally formed retaining feature, said polyethylene portion further including at least one pair of blind bores that extend from said posterior articulating surface toward said first inboard face and are separated by a bridge that is recessed inboard of said posterior articulating surface;

a porous metal portion having a radial sidewall extending between a uniformly convex anterior tissue engaging surface and a second inboard surface, said second inboard surface having a second integrally formed retaining feature comprising the other of said stem and recess centrally formed thereon and having the other of said annular central hub and said annular radial pocket; and wherein said first and second integrally formed retaining features cooperatively mate and said annular central hub and said annular radial pocket cooperatively mate around a mating surface that surrounds and is radially offset outboard a distance from said first and second integrally formed retaining features to resist separation of said polyethylene portion and said porous metal portion in an assembled position.

11. The patellar implant of claim 10 wherein said first integrally formed retaining feature includes said stem extending from a body of said polyethylene portion.

12. The patellar implant of claim 11 wherein said stem defines a proximal end extending from said body, an intermediate portion and a distal end, wherein a radius of said stem increases from said intermediate portion to said distal end.

13. The patellar implant of claim 12 wherein said second integrally formed retaining feature is defined by said recess formed in said porous metal portion, from said second inboard surface of said porous metal portion through an intermediate area to a terminal end, wherein a radius defined by said recess increases from said intermediate area to said terminal end.

14. The patellar implant of claim 10 wherein said polyethylene portion includes one of a protrusion and a depression that extends from said annular central hub or said annular radial pocket along said first inboard face.

15. The patellar implant of claim 14 wherein said protrusion comprises at least two protrusions and wherein said depression comprises at least two depressions and wherein said at least two protrusions define radial outset members defined on said first inboard surface of said polyethylene portion or said second inboard surface of said porous metal portion and wherein said at least two depressions define radial inset members defined on the other of said polyethylene portion and said porous metal portion.

16. The patellar implant of claim 10 wherein said annular central hub defines a radial projection that surrounds said stem and recess in said assembled position.

17. The patellar implant of claim 16 wherein said annular radial pocket defines a depression that is radially offset from said stem.

* * * * *